United States Patent [19]

Loeb

[11] 4,418,688

[45] Dec. 6, 1983

[54] MICROCATHETER HAVING DIRECTABLE LASER AND EXPANDABLE WALLS

[75] Inventor: Marvin P. Loeb, Chicago, Ill.

[73] Assignee: Laserscope, Inc., Arlington Heights, Ill.

[21] Appl. No.: 280,247

[22] Filed: Jul. 6, 1981

[51] Int. Cl.³ .............................................. A61B 1/00
[52] U.S. Cl. ................................................................ 128/6
[58] Field of Search ...................... 128/4, 5, 6, 7, 8, 9, 128/10, 11, 214.4

[56] References Cited

U.S. PATENT DOCUMENTS

| | | | |
|---|---|---|---|
| 3,897,775 | 8/1975 | Furihata | 128/6 |
| 4,040,413 | 8/1977 | Ohshiro | 128/6 |
| 4,066,071 | 1/1978 | Nagel | 128/7 |
| 4,146,019 | 3/1979 | Bass et al. | 128/6 |
| 4,207,874 | 6/1980 | Choy | 128/6 |
| 4,224,929 | 9/1980 | Furihata | 128/6 |
| 4,290,421 | 9/1981 | Siegmund | 128/6 |
| 4,313,431 | 2/1982 | Frank | 128/7 |

FOREIGN PATENT DOCUMENTS

| | | | |
|---|---|---|---|
| 2163653 | 6/1972 | Fed. Rep. of Germany | 128/4 |
| 2350382 | 4/1974 | Fed. Rep. of Germany | 128/6 |
| 2629828 | 1/1977 | Fed. Rep. of Germany | 128/4 |
| 2848484 | 5/1979 | Fed. Rep. of Germany | 128/6 |
| 2385372 | 3/1978 | France | 128/6 |

*Primary Examiner*—Kyle L. Howell
*Assistant Examiner*—Max F. Hindenburg

[57] ABSTRACT

A fiber optic microcatheter device is provided with a conduit directing system to tilt the distal end of an internal conduit with respect to an external tube held in a lumen by expanding the diameter of an elastic zone on the external tube. Within the internal conduit are viewing and illumination fiber optic bundles which permit viewing within the lumen. A laser light transmitting fiber within the internal conduit may be aimed at a site within the lumen by tilting the distal end of the internal conduit. Also provided are tubes for flushing and vacuum to provide clear viewing within the lumen and to remove debris.

22 Claims, 9 Drawing Figures

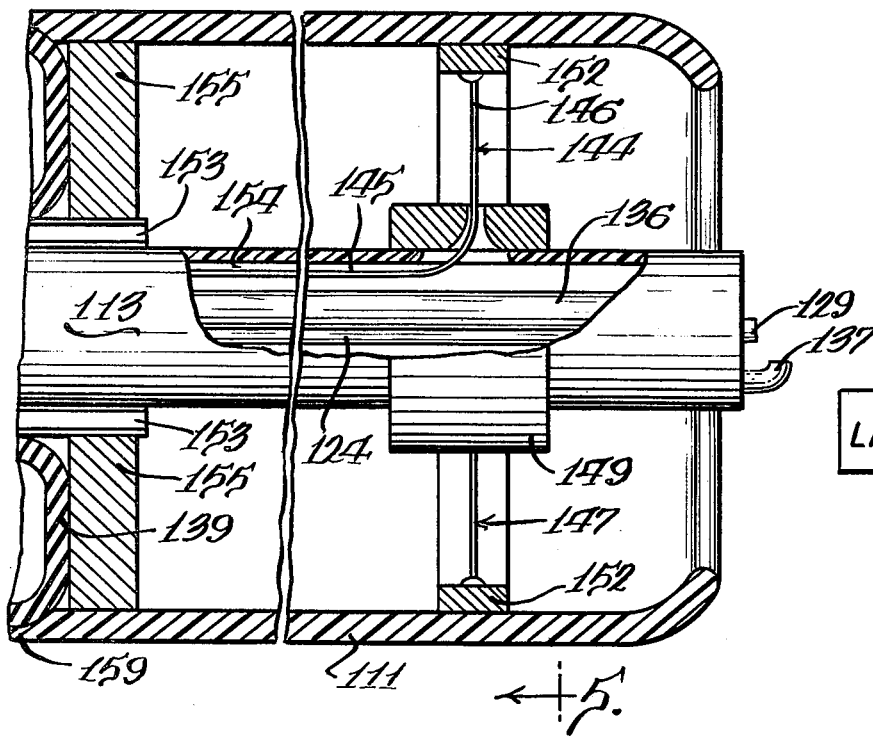
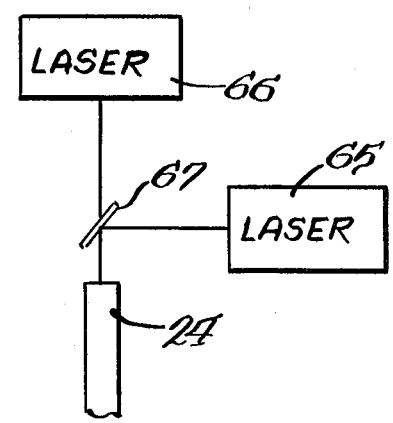
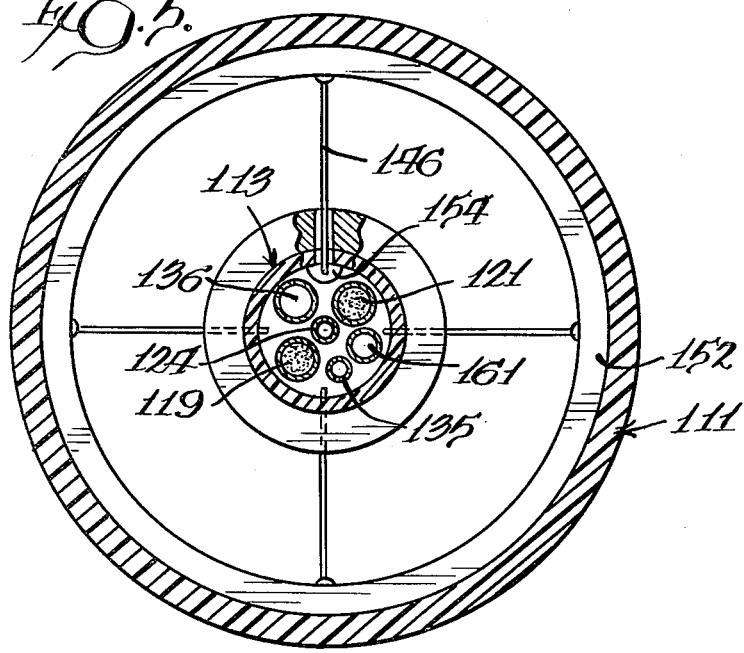
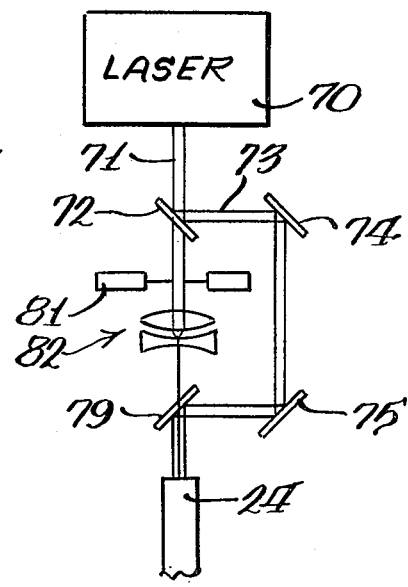

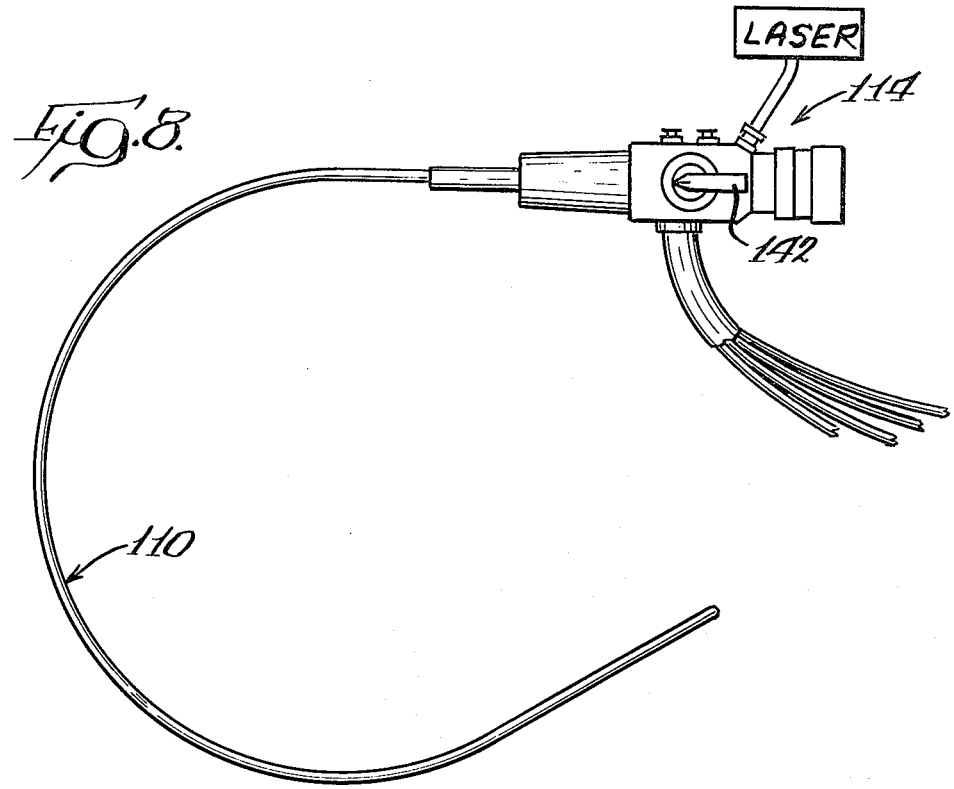
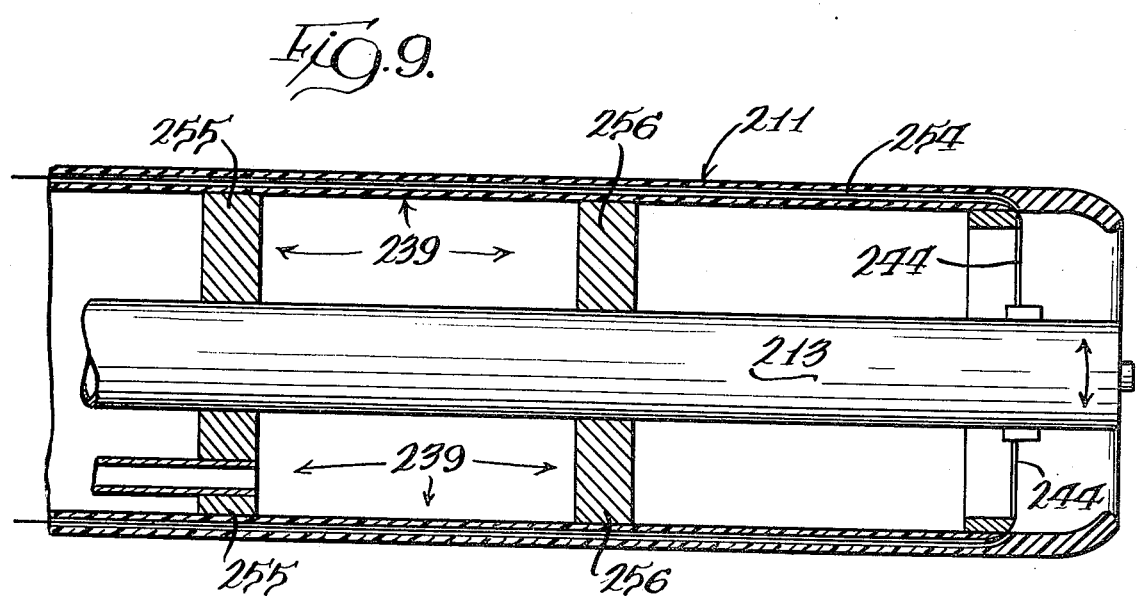

MICROCATHETER HAVING DIRECTABLE LASER AND EXPANDABLE WALLS

TECHNICAL FIELD

This invention relates to microcatheters and in particular microcatheters having fiber optic viewing bundles, coherent light transmitting fibers and expandable walls.

BACKGROUND OF THE INVENTION

Numerous proposals have been made for combining an endoscope i.e., a device having fiber optic viewing bundles for observation within a lumen of a patient, with a coherent, e.g. laser, light transmitting fiber. Illustrative of such devices are U.S. Pat. No. 4,146,019 to Bass et al. and U.S. Pat. No. 4,207,874 to Choy. However these inventions do not disclose methods for retaining such a combination within the lumen while the laser is being utilized, nor do they disclose means to direct the laser light to a particular site within the lumen.

The device disclosed in the patent to Choy is intended for use within an occluded blood vessel where the occlusion can be approached from the downstream side. In such an instant there is no blood flow to obstruct the surgeon's vision. However, the Choy device is inadequate in instances where a surgical procedure has to be performed on a blood vessel that still permits blood flow.

Accordingly, there exits a need for a device which combines the functions of an endoscope with a laser light transmitting fiber and which can seal off and flush a section of the lumen to allow a surgical procedure to be performed. Also desirable is a device having means to position the laser light transmitting fiber within the lumen so as to direct the transmitted laser light to a particular site with the lumen. The device of the present invention fulfills both of the foregoing objectives.

SUMMARY OF THE INVENTION

The present invention provides a fiber optic microcatheter device suitable for performing medical procedures in a lumen within a patient. The device includes a microcatheter having a distal end to be inserted into a patient and a control handle held by a surgeon to direct the contemplated procedure. The microcatheter has an elongated external tube having an elastic zone spaced from the distal end, an internal conduit containing one or more fiber optic viewing bundles and a coherent, e.g., laser, light transmitting fiber. The microcathether may also be provided with one or more fluid passageways through which gases or liquids may be evacuated or transmitted. The elastic zone of the external tube is expandable. Preferably, at least one expandable balloon is located between the internal conduit and the external tube adjacent to the elastic zone. Expansion of the balloon increases the diameter of the elastic zone until it contacts the walls of the lumen and forms a seal.

A substantially rigid collar is located between the elastic zone and the distal end within and in contact with the external tube. A conduit directing system cooperates with the collar to tilt the distal end of the internal conduit with respect to the external tube. This directs laser light emitted from the fiber to a particular site within the lumen.

The conduit directing system comprises one or more cables each having a control length portion and a directing length portion. The directing length portion is located between the internal conduit and the collar. Placing tension on the control length portion shortens the directing length portion and tilts the distal end of the internal conduit with respect to the external tube. Preferably a plurality of cables, e.g., four cables, is used to direct the tilting of the internal conduit.

In one embodiment, one end of the directing length portion is fixed on the internal conduit and then extends to the collar. The control length portion then passes through a cable guide within the collar and down through a cable tube between the internal conduit and the external tube. The cable tube may be located between the external tube and the expandable balloon, between the balloon and the internal conduit or within the wall of the external tube. Alternatively, one end of the directing length portion is fixed on the collar and then extends to the internal conduit. The control length portion then passes through a channel within the internal conduit. In both cases, the control length portion of the cable extends to a control means such as a knob or joystick, which places tension on the control length portion, shortens the directing length portion and tilts the distal end of the internal conduit with respect to the external tube.

A plurality of fluid passageways can be located within the internal conduit to serve as suction and flushing passageways. The cable tube between the internal catheter and external tube can also serve as a suction or flushing passageway.

In use, the surgeon obtains access to a lumen such as a blood vessel by making an incision at an appropriate site on a patient. The microcatheter is then inserted into the blood vessel and fluoroscopically tracked until the distal end thereof reaches the vicinity of the operation site. The elastic zone of the external tube is expanded against the walls of the lumen, sealing off the area. A combination of suction and saline flushing is applied through the passageways in the internal catheter or the cable tubes to provide a clear view of the operation site.

After the operation site has been visually located, tension is applied to one or more cables to tilt the distal end of the internal conduit to aim the laser light transmitting fiber. During aiming a relatively low level laser light may be transmitted through the fiber to enable the operator to determine if the fiber is properly aimed. After it has been determined that the fiber has been properly aimed, an intense laser light pulse is transmitted through the fiber striking the operation site. Loose debris and vapor which may be produced can be flushed and removed through the suction passageway within the internal conduit. The balloon is then deflated and the microcatheter is removed from the patient.

Numerous other advantages and features of the present invention will become readily apparent from the following detailed description of the invention, the accompanying examples, and the appended claims.

BRIEF DESCRIPTION OF THE DRAWINGS

FIG. 4 is similar to FIG. 2, but showing the conduit directing system operating generally from within the internal conduit;

FIG. 5 is an enlarged cross-sectional view taken along plane 5—5 of FIG. 4 showing the interior structure of the internal conduit;

FIG. 6 is a graphic representation of a laser source for the present invention;

FIG. 7 is a graphic representation of an alternative laser source suitable for use with the present invention;

FIG. 8 is an illustration of a device similar to FIG. 1 but having a joystick on the handle; and FIG. 9 is a fragmentary view of a device similar to FIG. 2, but lacking a separate balloon and having cables passing through channels in the wall of the external tube.

DETAILED DESCRIPTION OF THE PREFERRED EMBODIMENTS

Figure 1:
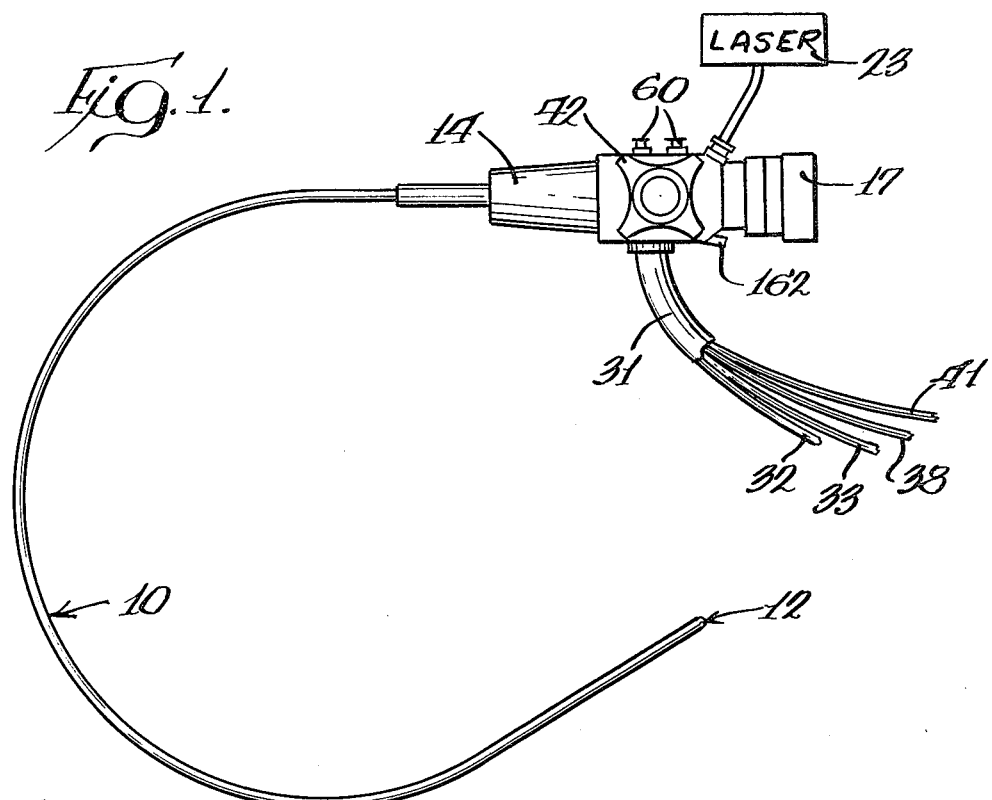
FIG. 1 is an illustration of a device embodying the present invention and having a microcatheter with a distal end which can be inserted into a patient and a control handle with knobs.

While this invention is susceptible of embodiment in many different forms, there are shown in the drawings and will be described in detail, preferred embodiments of the invention. It should be understood, however, that the present disclosure is considered as an exemplification of the principles of the invention and is not intended to limit the invention to the embodiments illustrated.

The precise shape and sizes of the components described are not essential to the invention unless otherwise indicated. The apparatus of this invention may utilize certain conventional cable tension control mechanisms and fiber optic systems, the details of which, though not fully illustrated or described, will be apparent to those having skill in the art and an understanding of the necessary functions of such mechanisms.

Figure 2:
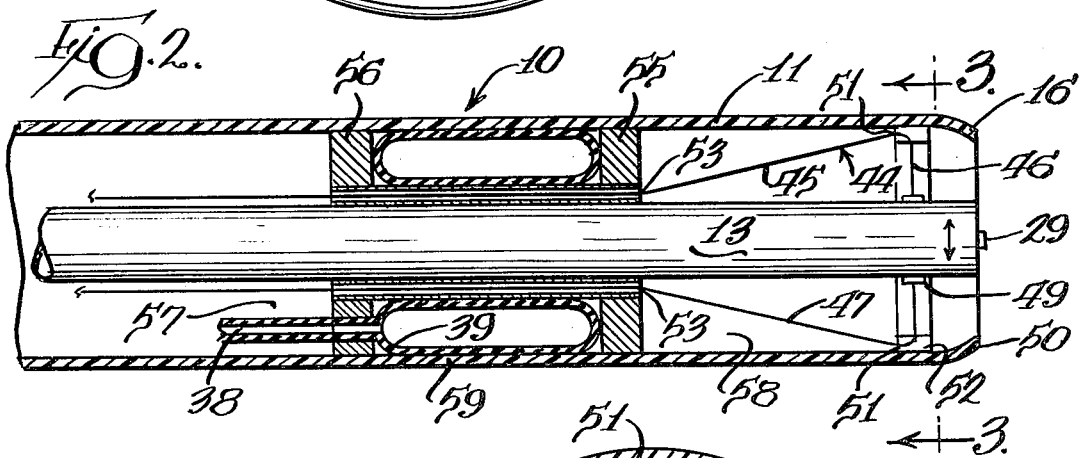
FIG. 2 is an enlarged, fragmentary cross-sectional view of the distal end of the microcatheter showing an internal conduit within an external tube together with an expandable balloon and a conduit directing system.
Figure 3:
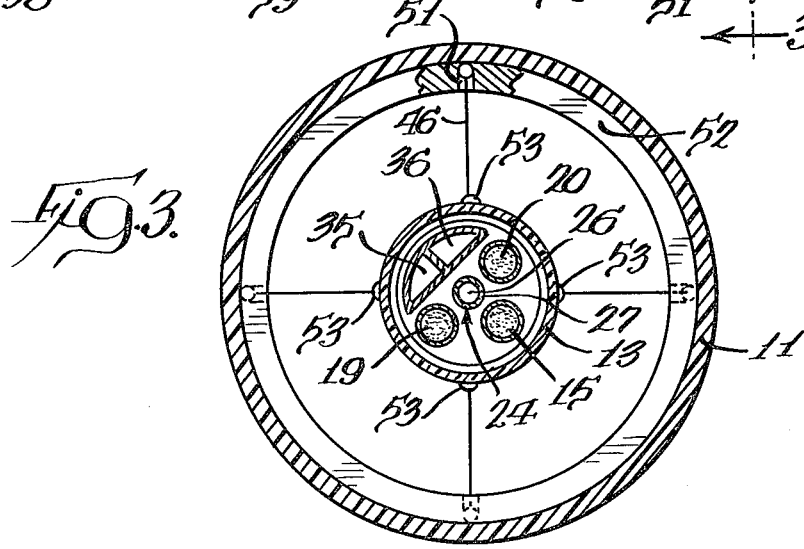
FIG. 3 is an enlarged, cross-sectional view taken along plane 3—3 of FIG. 2 showing a laser light transmitting fiber and a fiber optic viewing bundle together with auxiliary elements within the internal conduit.

Referring to FIGS. 1–3, the fiber optic microcatheter device of the present invention comprises an elongated microcatheter 10 having a distal end 12 adapted to be inserted into a patient and a control handle 14 which is manipulated by a surgeon. The microcatheter is flexible and generally comprises an internal conduit 13 having a distal end (FIG. 2) within an elongated external tube 11 constructed of a flexible material and having a distal end 16. A light source is mounted in control handle 14 and provides illumination to the distal end 12 through an illumination fiber bundle 15 (FIG. 3). A viewing system is also mounted in the control handle with eye piece 17 for viewing through the distal end 12 via one or more fiber optic viewing bundles 19 and 20. Additional fiber optic bundle 20 may be supplied to serve as a further light source or as an alternative viewing bundle should viewing bundle 19 become obstructed. The illumination and fiber optic viewing bundles together with the light source and optics may be conventional in design.

Provision is made for delivering laser light to the distal end 12 of the microcatheter 10. A laser light source 23 directs laser light into the control handle 14 which in turn directs the light through a laser light transmitting fiber 24 located within the internal conduit 13 (FIG. 3). Preferably a single glass fiber 26 with a diameter of about 100 to about 200 microns surrounded with a protective sheath 27 is utilized for the laser light transmitting fiber 24. It is desirable to use a single glass fiber as opposed to a bundle of fibers. Intense laser radiation has a tendency to destroy the cement between individual fibers in a bundle, rendering the bundle inoperative.

A replaceable transparent window 29 is positioned at the distal end of the fiber 24 to protect the end of the fiber. Preferably the window is of glass or quartz and may include a lens to focus the laser light at a specific distance. Should the window become damaged, it may be replaced, avoiding the costly necessity of replacing the entire laser light transmitting fiber 24.

When using the present invention in a lumen which contains an opaque fluid such as blood, it is necessary to remove the opaque fluid and flush the area with a clear fluid such as saline to provide clear viewing. To accomplish this, a tube assembly 31 is mounted on the control handle 14 (FIG. 1). The tube assembly includes a suction tube 32 and fluid flushing tube 33 in fluid communication with fluid passageways 35 and 36 within the internal conduit 13. Included in the tube assembly 31 is a hose 38 in fluid communication with an expandable balloon 39 located within the external tube 11. The operation of the expandable balloon is described in detail below. Also mounted in the tube assembly 31 is an additional fluid tube 41 which may be connected to one or more channels or tubes within the external tube 11 as described in more detail below. Additional tubes may be added to the tube assembly 31 as needed.

The control handle 14 may be provided with push buttons 60 which can control valves for any of the fluid passageways in the conduit 13 or can regulate the operation of the laser.

To direct the transmitted laser light to a particular site within the lumen, the present invention is equipped with a conduit guidance or directing system to tilt the distal end of the internal conduit 13 with respect to the external tube 11. The conduit directing system includes a pair of knobs 42 mounted on each side of the control handle 14 (FIG. 1) and at least one cable 44 (FIG. 2). The cable may be a monofilament line, wire, thread, or any other such linear connector. A substantially rigid collar 52 is located within and in contact with the external tube 11. The collar 52 helps retain the shape of the external tube 11 and cooperates with the conduit directing system when the distal end of the internal conduit is tilted. A flexible, inwardly curved nose piece 50 of external tube 11 helps guide the catheter 10 through the lumen.

The cable 44 has a directing length portion 46 defined by that portion of the cable between the collar 52 and internal conduit 13. A control length portion 45 comprises the remainder of the cable 44. As one of the knobs 42 is turned, tension is placed along the control length portion 45 of one cable 44 while tension is released in another cable 47 opposite with respect to the internal conduit 13. Such a tension control device is disclosed in U.S. Pat. No. 4,203,430 to Takahashi and is incorporated by reference herein. The tension in the control length portion 45 reduces the length of the directing length portion 46 between the internal conduit 13 and the collar 52, causing the distal end of the internal conduit to tilt with respect to the external tube.

Alternatively, as shown in FIG. 8, the knobs may be replaced by a joystick 142 mounted on the control handle 114. The joystick would be connected to the cables as is known in the art so that movement of the joystick will correspond to a directional tilting of the internal conduit within the microcatheter 110.

Although two pair or four cables are shown in the FIGURES, any number of cables may be used, but at least three are preferred. Only one cable need be used to tilt the internal conduit 13. The internal conduit preferably has enough resiliency to return to its center rest position when tension is released from the cable.

In FIG. 2, one end of the directing length portion 46 of the cable is fixed on a ring 49 which extends peripherally about the internal conduit 13. The cable then extends from the ring 49 through a guide 51 in the collar 52. The cable 44 then extends from the guide 51 through the external tube 11 to a cable tube 53 which extends between bulkheads 55 and 56 spaced from each other whereupon the cable 44, and in particular the control length portion 45, extends to the control handle 14. The cable tube 53 may be located between the internal conduit 13 and balloon 39 as shown in FIG. 2, or may be located between the balloon and external tube 11 or may be integral with the external tube or with the balloon.

The cable tube can be replaced by channel 254 in the wall of the external tube 211 as can best be seen in FIG. 9. As before, tension on cables 244 causes internal conduit 213 to tilt with respect to the external tube 211. The cable directing system may be provided with means to provide slack to all cables 244 while the expanding means 239 defined by a portion of the external tube 211 and bulkheads 255 and 256 is inflated.

If desired, the additional fluid tube 41 shown connected to the tube assembly 31 (FIG. 1) may be put in fluid communication with annular space 57 between the internal conduit 13 and the external tube 11. The cable tubes 53 are in fluid communication with the annular space 57 and a distal annular space 58 defined by the distal end 16 of the external tube 11 and the internal conduit 13. Introducing a vacuum or fluid pressure into the annular space 57 flushes or removes any obstructions within the cable tubes 53. Such flushing will also remove obstructions from a distal annular space 58. Since a piece of matter lodged within the distal annular space 58 could interfere with the tilting of the internal conduit, such an arrangement is desirable.

To seal off the lumen and fix the position of the external tube 11 with respect to the lumen, the external tube is provided with a peripheral elastic expandable zone 59. An expanding means such as expandable balloon 39 is associated with zone 59 to increase its diameter. When the expandable balloon 39 is inflated, the elastic zone 59 increases in diameter and contacts the lumen to form a seal. The bulkheads 55 and 56 maintain the proper centering of the internal conduit 13 as well as maintaining the proper positioning of the expandable balloon 39. Alternatively, a plurality of balloons may be used in place of a single balloon or the bulkheads and the expandable zone may define the expanding means as shown in FIG. 9.

Locating the expanding means or balloon within the external tube 111 has a particular advantage. The elastic zone 59 and the remainder of the external tube wall present a smooth surface which is less likely to damage the lumen as the microcatheter is inserted. Inflatable balloons on the outside of the external tube would present surfaces which could become snagged as the distal end of the microcatheter attempts to make its way around a curve or juncture in the lumen. The structure of the present invention avoids this problem.

An alternative embodiment is shown in FIGS. 4 and 5. In this embodiment the conduit directing system comprises a cable 144 having a directing length portion 146, one end of which is fixed on a substantially rigid collar 152 and extends to the internal conduit 113. The cable 144 also has a control length portion 145 which extends into the internal conduit 113 through channels 154 to the control handle 14. The channels 154 may be defined by the space remaining in the internal conduit 113 about the fluid passageways and fiber optic bundles or may be defined by separate tubes within the internal conduit 113. The internal conduit 113 may be provided with ring 149 to guide the cable 144 to the conduit 154. This embodiment has the advantage that less cable is exposed between the internal conduit 113 and the external tube 111, thus reducing the possibility of interference to the operation of the conduit directing system.

Also shown in this embodiment is the peripheral elastic expandable zone 159 being of a different material and thickness than the rest of the external tube 111. As balloon 139 is expanded between bulkheads 155 and 156, it causes zone 159 to expand in diameter to contact and seal with the lumen. The balloon 139 is expanded by being inflated with a fluid e.g., gas or liquid through the hose such as carbon dioxide or saline solution.

As before, when tension is placed on one cable e.g. 146, while tension is released on an opposite cable, e.g. 147, the distal end of the internal conduit 113 is tilted with respect to the external wall 111. Similar to before, the internal conduit 113 houses a fiber optic viewing bundle 119, a laser light transmitting fiber 124 and an illumination fiber bundle 121. Also included in this embodiment within the internal catheter 113 is a flushing passageway 135 and a suction passageway 136. The flushing passageway 135 has on its end a cowl 137 to direct the flow of flushing over the ends of the viewing bundle 119 and the laser window 129. This not only flushes the inside of the lumen but helps to remove any obstructions which may become deposited on the ends of either the viewing bundle or the laser light transmitting bundle.

The internal conduit also houses an access hose 161 which allows an instrument (not shown) such as a suction tube, a tube with a needle, or miniature medical forceps to be inserted into the control handle end of the hase 162 and through the internal conduit. The conduit directing system is then utilized to direct the instrument to a particular site within the lumen. Tubes 153 may be present to serve the same flushing and suction purposes of the cable tubes 53 of FIG. 2.

Because the cable design of the present invention operates by tilting the distal end of the internal conduit with respect to the external tube, it has the particular advantage of allowing fine manipulation and accurate aiming of the components carried within the internal conduit. This accurate aiming of fine manipulation, not present in prior art devices which were generally for viewing or had an untilting laser catheter, is particularly important in the device of the present invention. Because this invention may be used to remove a growth, plaque or thrombus from a wall on a lumen, it is particularly important that the aim be precise to prevent unnecessary damage to the lumen.

FIG. 6 shows a graphic illustration of an alternative embodiment for the laser light source 23. In this embodiment a relatively low intensity guidance laser 65 and a relatively high intensity operating laser 66 are optically joined by a partially reflective mirror 67 to direct their respective beams into the laser light transmitting fiber 24. The directing laser may be a continuous laser while the operating laser may be an intermittent laser. The partially reflective mirror 67 can be partially silvered to allow only some of the directing laser light to be reflected into the laser light transmitting fiber 24 while transmitting approximately 90% of the operating laser light into the fiber. The directing laser is used to project a spot in the lumen indicating where the laser light transmitting fiber is aimed. After it has been determined that the device is properly aimed, the operating laser 66 is then activated.

Alternatively the laser source 23 may comprise those components seen in FIG. 7. Laser 70 produces an initial broad beam of laser light 71 which is partially reflected by mirror 72. The reflected portion 73 of the beam is again reflected by two guide mirrors, 74 and 75 and again reflected by a second partial mirror 79. This reflected beam is then reflected into the laser light transmitting fiber 24 to serve as a guidance beam. Because mirrors 72 and 79 only reflect about 10 to 20 percent of the light striking them, the guidance beam will only have an intensity of 1 to 4 percent of the initial beam 71.

The light transmitted through partial mirrors 72 and 79 is an operating beam which passes through beam interrupting means or shutter 81 and collimating optics 82 to form a small diameter beam 84 which is transmitted to the fiber 24. Alternatively an optic fiber may be used to replace mirrors 74 and 75 or direct part of the broad beam 71 around the shutter 81. The shutter 81 may also be set so as not to completely close, the transmitted part of the beam serving as a directing beam.

This embodiment has the advantage of using a single laser to provide a guidance beam and when the shutters 81 are open, an operating beam. The laser 70 may be mounted outside the control handle 14 with the mirrors, shutter, and optics within the handle with the shutter controlled by one of the push buttons 60.

The operating laser may be any suitable laser such as ruby rod, argon, or neodymium-YAG (yttrium-aluminum-garnet) laser or the like. Preferably however, an argon or neodymium-YAG (5320 Angstroms) laser is used. The blue-green wavelength is particularly useful for blood coagulation. While any effective power level can be used, generally 1 to 5 watts is effective.

The directing laser may be of the same type as the operating laser or may also be a helium-neon or kryton laser or any other suitable light source. The directing laser need only be in the milliwatt range with the color chosen to be that best visible as a guidance beam within the lumen.

In operation, the catheter 10 inserted into a lumen within a patient and directed to the general area where the surgical procedure is to be performed. The position of the distal end 12 of the catheter 10 can be determined by making the collar 52 out of a radiologically opaque material and monitoring its position by use of a fluoroscope as the catheter is inserted. After the distal end of the catheter has reached the desired position within the patient, a fluid such as carbon dioxide or saline is introduced into the hose 38 to expand the balloons 39 until the peripheral elastic zone contacts the walls of the lumen.

After the catheter has been fixed in place, a combination of flushing and suction is used to provide clear viewing. The directing laser is then activated and the cable directing system is used to aim the directing laser beam at a site within the lumen such as a growth, polyp, plaque or thrombus. After the beam is properly aimed, the operating laser is activated and the site is struck by a high intensity laser beam. Any debris or gas produced can be removed through the suction tubes and the site can be flushed with saline and the site viewed to determine that the desired effect has been obtained. Alternatively, a suction tube or miniature medical forceps may be inserted through the access hose 61 and directed to remove material such as part of a thrombus.

The foregoing specification is intended as illustrative and is not to be taken as limiting. Still other variations within the spirit and scope of this invention are possible and will readily present themselves to those skilled in the art.

What is claimed is:

1. A fiber optic microcatheter device suitable for performing medical procedures in a lumen within a patient, the microcatheter device comprising:
   (a) an elongated external tube constructed of a flexible material, having a distal end and a peripheral elastic, expandable zone spaced from the distal end;
   (b) an elongated flexible internal conduit having a distal end proximate to the distal end of the external tube and positioned within the external tube;
   (c) at least one fiber optic viewing bundle located within the internal conduit and substantially coterminous with the distal end of the internal conduit to permit viewing within the lumen.
   (d) at least one laser light transmitting fiber located within the internal conduit and substantially coterminous with the distal end of the internal conduit to permit propagation of laser light through the conduit to a site within the lumen;
   (e) expanding means associated with the elastic, expandable zone for increasing the outside diameter of the zone so as to form a liquid seal with the lumen;
   (f) a substantially rigid collar inside and in contact with the external tube, the collar located between the elastic zone and the distal end of the external tube; and
   (g) a conduit directing system including at least one cable having a directing length portion between the internal conduit and the collar such that shortening of the directing length portion tilts the distal end of the internal conduit with respect to the external tube, the cable also including a control length portion attached to the directing length portion to shorten the directing length portion.

2. The microcatheter device of claim 1 wherein the internal conduit further defines a fluid passageway along the length of the internal conduit.

3. The microcatheter device of claim 2 wherein the internal conduit further defines a plurality of fluid passageways along the length of the internal conduit.

4. The microcatheter device of claim 1 wherein the collar is integral with the external tube.

5. The microcatheter device of claim 1 including at least three cables to tilt the internal conduit.

6. The microcatheter device of claim 1 wherein the expanding means conprises at least one expandable balloon extending substantially about the periphery of the internal catheter and within the external tube adjacent the elastic zone.

7. The microcatheter device of claim 1 including at least one cable tube is located between the external tube and the internal conduit and the control length portion of the cable passes through the cable tube and one end of the directing length portion of the cable is fixed on the internal conduit.

8. The microcatheter device of claim 1 wherein the internal conduit further defines at least one channel into which the control length portion of the cable passes, and one end of the directing length portion of the cable is fixed on the collar.

9. The microcatheter device of claim 1 including an operating laser light source operably associated with the laser light transmitting cable to perform a medical procedure within the lumen and a control handle to place tension in the control length portion of the cable to shorten the directing length portion, the handle also retaining viewing optics operably associated with the viewing bundle.

10. The microcatheter device of claim 9 including a directing laser light source operably associated with the light transmitting cable to determine the aiming of the light transmitting fiber.

11. The microcatheter device of claim 1 wherein the external tube defines at least one channel into which the control length portion of the cable passes, and one end of the directing length portion of the cable is fixed on the internal conduit.

12. The microcatheter device of claim 1 wherein the expanding means is defined by the expandable zone of the external tube and by two bulkheads spaced from each other within the external tube.

13. A fiber optic microcatheter device suitable for performing medical procedures in a lumen within a patient, the microcatheter device comprising:
  (a) an elongated external tube being constructed of a flexible material and having a distal end and a peripheral elastic zone spaced from the distal end;
  (b) an elongated flexible internal conduit having a distal end proximate to the distal end of the external tube and positioned within the external tube;
  (c) at least one fiber optic viewing bundle located within the internal conduit and substantially coterminous with the distal end of the internal conduit to permit viewing within the lumen;
  (d) at least one laser light transmitting fiber located within the internal conduit and substantially coterminous with the distal end of the internal conduit to permit propagation of laser light through the conduit to a site within the lumen;
  (e) at least one expandable balloon extending substantially about the periphery of the internal catheter and within the external tube adjacent the elastic zone, the balloon when expanded cooperating with the elastic zone to increase the exterior diameter of the elastic zone to contact the lumen;
  (f) a substantially rigid collar inside and in contact with the external tube, the collar located between the elastic zone and the distal end of the external tube, the collar also defining at least one cable guide;
  (g) at least one cable tube extending for at least the length of the expandable balloon and located between the internal conduit and the external tube; and
  (h) a cable, one end of which is fixed to the internal conduit, the cable extending from the internal conduit about the cable guide and through the cable tube such that when tension is placed on the cable, the distal end of the internal conduit is tilted with respect to the external tube.

14. The microcatheter device of claim 13 including at least three cable tubes, three cable guides, and three cables to tilt the internal conduit.

15. The microcatheter device of claim 13 where the internal conduit further defines at least one fluid passageway along the length of the internal conduit.

16. The microcatheter device of claim 13 including an operating laser light source operably associated with the laser light transmitting cable to perform a medical procedure within the lumen and a control handle to place tension in the cable and retaining viewing optics operably associated with the viewing bundle.

17. A fiber optic microcatheter device suitable for performing medical procedures in a lumen within a patient, the microcatheter device comprising:
  (a) an elongated external tube being constructed of a flexible material and having a distal end and a peripheral elastic zone spaced from the distal end;
  (b) an elongated flexible internal conduit having a distal end and defining at least one channel, and positioned within the external tube;
  (c) at least one fiber optic viewing bundle located within the internal conduit and substantially coterminous with the distal end of the internal conduit to permit viewing within the lumen;
  (d) at least one laser light transmitting fiber located within the internal conduit and substantially coterminous with the distal end of the internal conduit to permit propagation of laser light through the conduit to a site within the lumen;
  (e) at least one expandable balloon extending substantially about the periphery of the internal catheter and within the external tube adjacent the elastic zone, the balloon when expanded cooperating with the elastic zone to increase the exterior diameter of the elastic zone to contact the lumen;
  (f) a substantially rigid collar inside and in contact with the external tube, the collar being located between the elastic zone and the distal end of the external tube; and
  (g) at least one cable extending from a fixed point on the collar through the channel in the internal conduit such that when tension is placed on the cable, the distal end internal conduit is tilted with respect to the external tube.

18. The microcatheter device of claim 17 including at least three channels and three cables to tilt the internal conduit.

19. The microcatheter device of claim 17 where the internal conduit further defines at least one fluid passageway along the length of the internal conduit.

20. The microcatheter device of claim 17 including an operating laser light source operably associated with the laser light transmitting cable to perform a medical procedure within the lumen and a control handle to direct tension in the cable and retaining viewing optics operably associated with the viewing bundle.

21. A method of performing a surgical procedure on the internal walls of a lumen within a patient, the method comprising:
  (a) preparing an access site to the lumen;
  (b) inserting through the access site into the lumen a microcatheter having an external tube, an internal conduit within the external tube, viewing fiber optics, fluid passageways, a laser light transmitting fiber carried by the internal conduit, a conduit directing system having cables to tilt the internal conduit with respect to the external tube, and an inflatable balloon within the external tube;
  (c) inflating the balloon to expand the diameter of a portion of the external tube to seal with the lumen and fix the position of the microcathether within the lumen;

(d) using a combination of suction and flushing with a clear fluid through the fluid passageways to provide an unobstructed view within the lumen for the viewing fiber optics;

(e) placing tension on one or more cables of the conduit directing system to tilt the internal conduit to aim the laser light transmitting fiber at a site within the lumen;

(f) transmitting an operating beam of laser light through the laser light transmitting fiber to the site within the lumen;

(g) using a combination of flushing and suction to remove any debris liberated after the laser light is transmitted; and (h) deflating the balloon and removing the microcatheter from the patient.

22. The method of claim 21 including transmitting a low intensity laser light through the laser light transmitting fiber while the conduit directing system is used to properly aim the fiber.

* * * * *